(12) United States Patent
Osypka

(10) Patent No.: US 7,151,965 B2
(45) Date of Patent: Dec. 19, 2006

(54) DEVICE AND METHOD FOR DELIVERING CARDIAC LEADS

(75) Inventor: Thomas P. Osypka, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 516 days.

(21) Appl. No.: 10/623,206

(22) Filed: Jul. 18, 2003

(65) Prior Publication Data

US 2004/0054388 A1     Mar. 18, 2004

Related U.S. Application Data

(60) Provisional application No. 60/397,203, filed on Jul. 19, 2002.

(51) Int. Cl.
*A61N 1/04* (2006.01)
(52) U.S. Cl. ...................................... 607/116; 604/264
(58) Field of Classification Search ................ 607/116, 607/119, 120, 122, 126–128; 606/129; 600/108, 600/129, 585; 604/160, 165.01, 165.02
See application file for complete search history.

(56) References Cited

U.S. PATENT DOCUMENTS

| 4,209,019 | A | * | 6/1980 | Dutcher et al. | ............. | 607/127 |
| 4,644,957 | A | * | 2/1987 | Ricciardelli et al. | ........ | 600/376 |
| 4,972,847 | A | * | 11/1990 | Dutcher et al. | ............. | 607/131 |
| 5,003,990 | A |   | 4/1991 | Osypka | | |
| 5,242,431 | A | * | 9/1993 | Kristiansen | .................. | 604/533 |
| 5,500,012 | A | * | 3/1996 | Brucker et al. | ............. | 607/122 |
| 6,095,981 | A | * | 8/2000 | McGahan | ................... | 600/461 |
| 6,185,464 | B1 |  | 2/2001 | Bonner et al. | | |
| 6,213,988 | B1 | * | 4/2001 | McIvor et al. | .............. | 604/264 |
| 6,551,269 | B1 | * | 4/2003 | Clemens et al. | .............. | 604/19 |

* cited by examiner

*Primary Examiner*—Robert E. Pezzuto
*Assistant Examiner*—Eric D. Bertram
(74) *Attorney, Agent, or Firm*—Scott D. Wofsy; Edwards Angell Palmer & Dodge LLP

(57) ABSTRACT

A cardiac lead delivery device is disclosed which includes an elongated carrier body having opposed proximal and distal end portions and defining an interior channel for accommodating implantable cardiac leads, and an adjustable collar for securing the implantable cardiac leads within the interior channel of the carrier body during delivery to an implantation site.

5 Claims, 6 Drawing Sheets

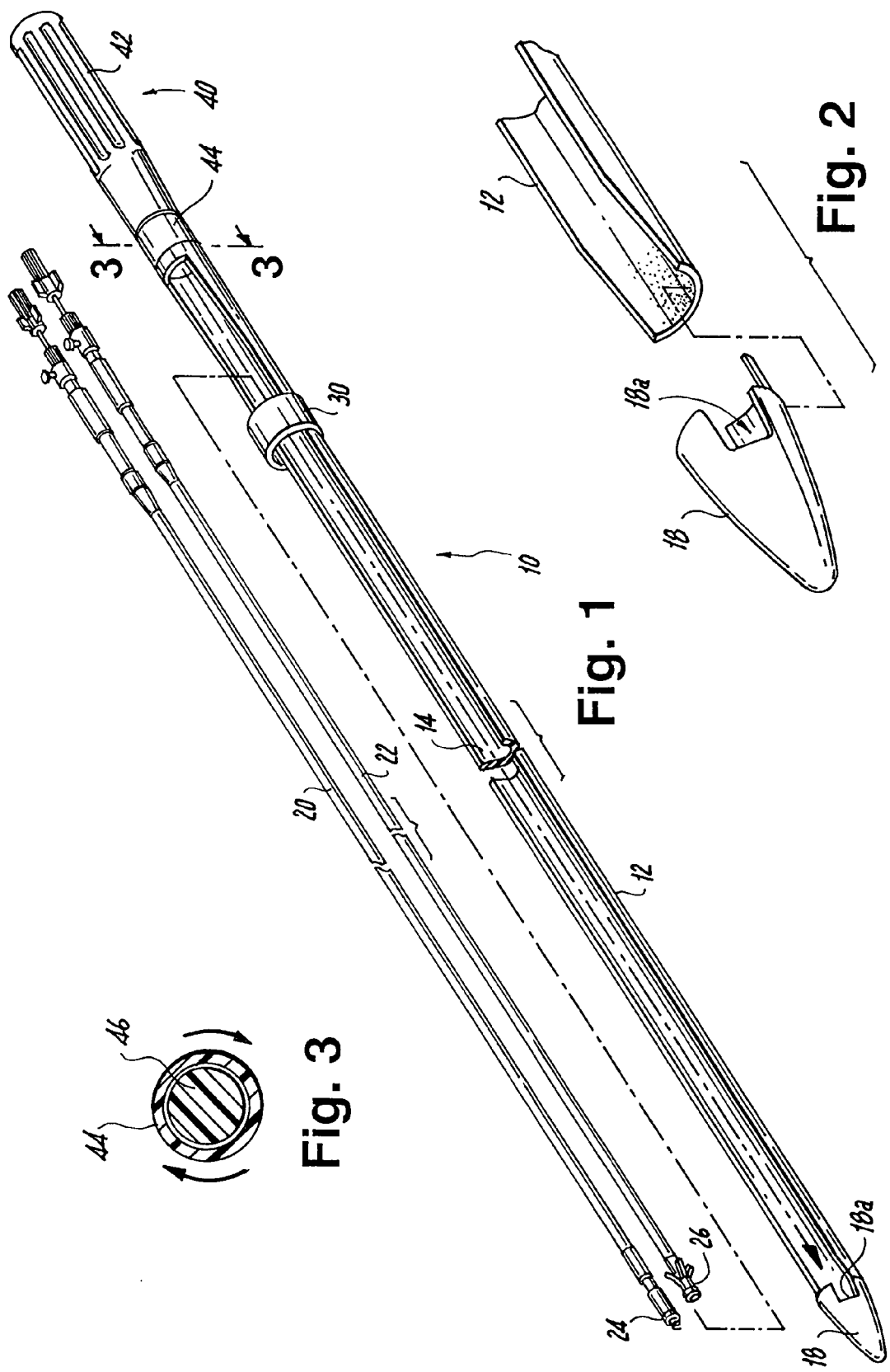

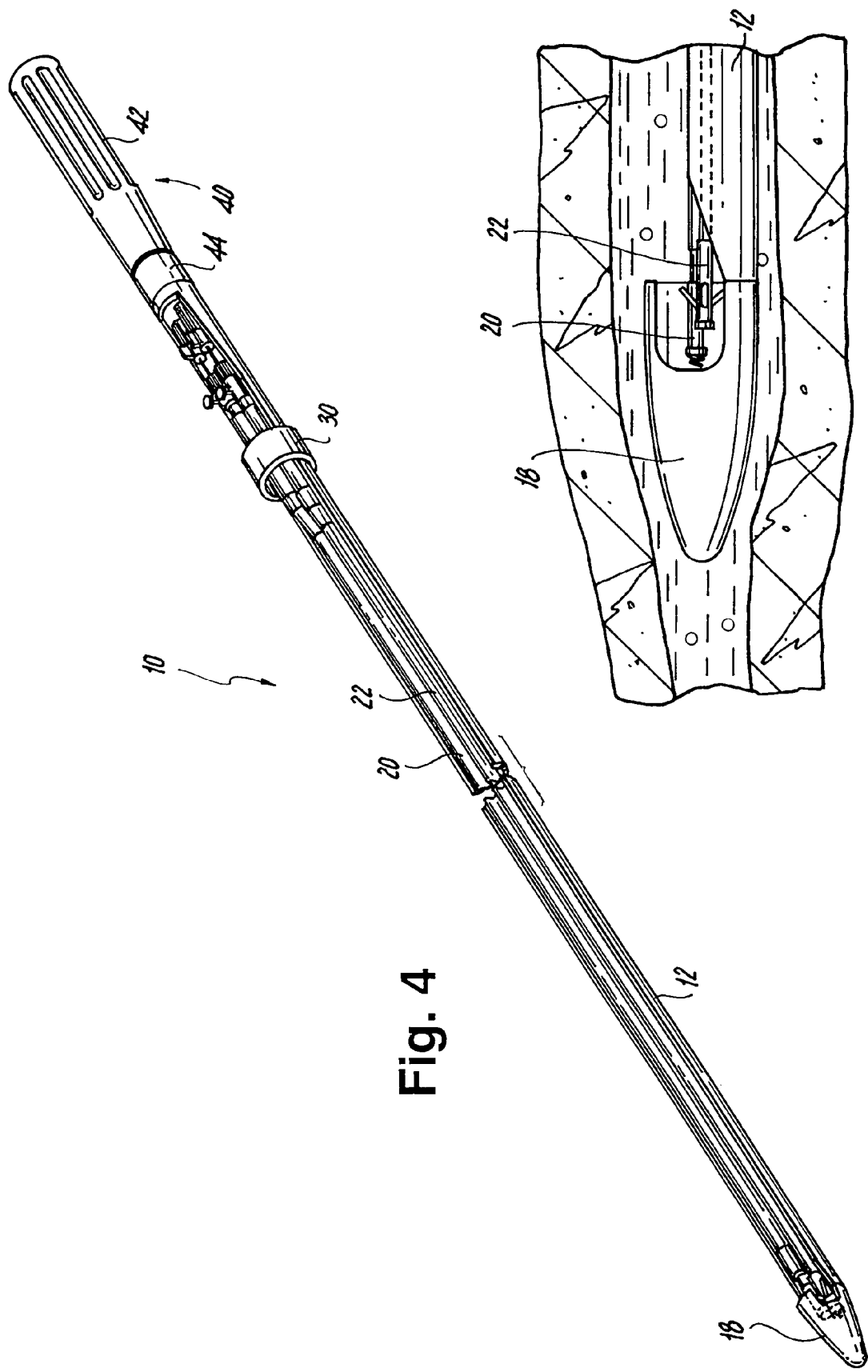

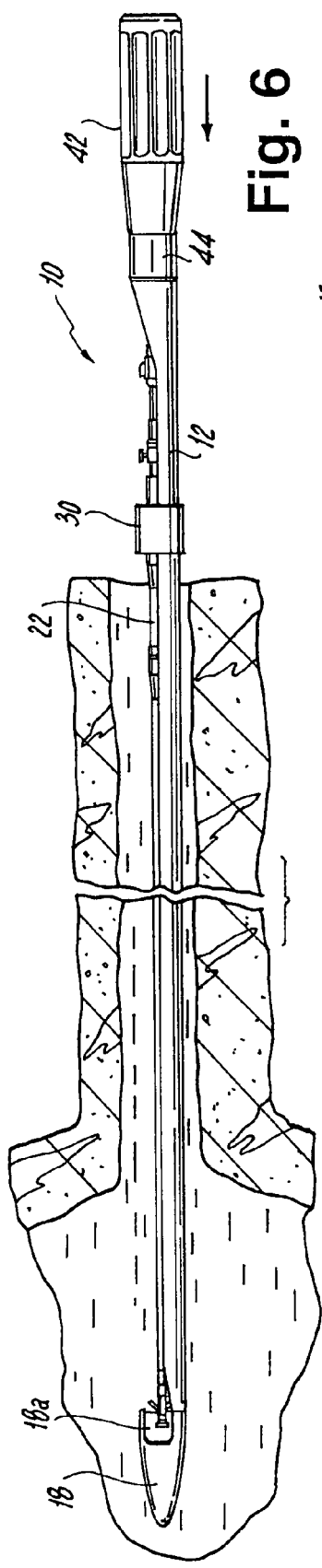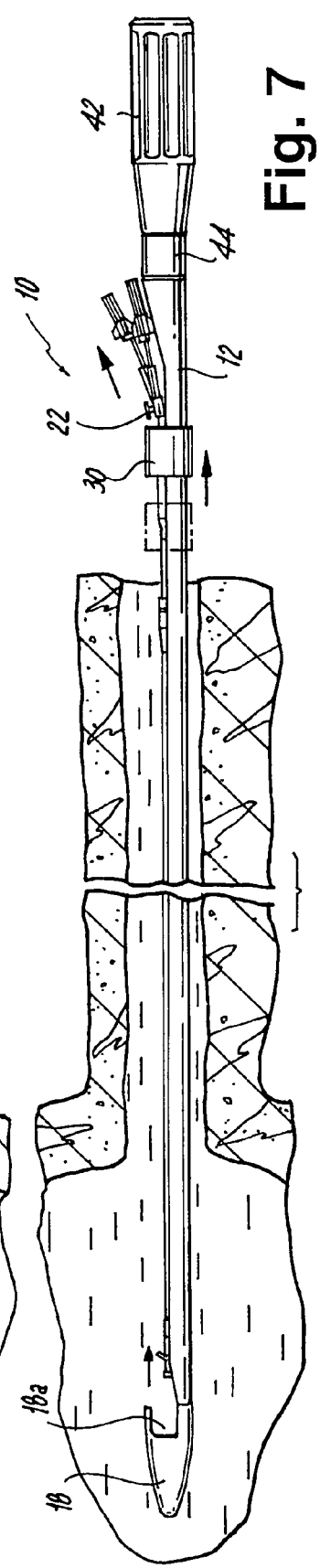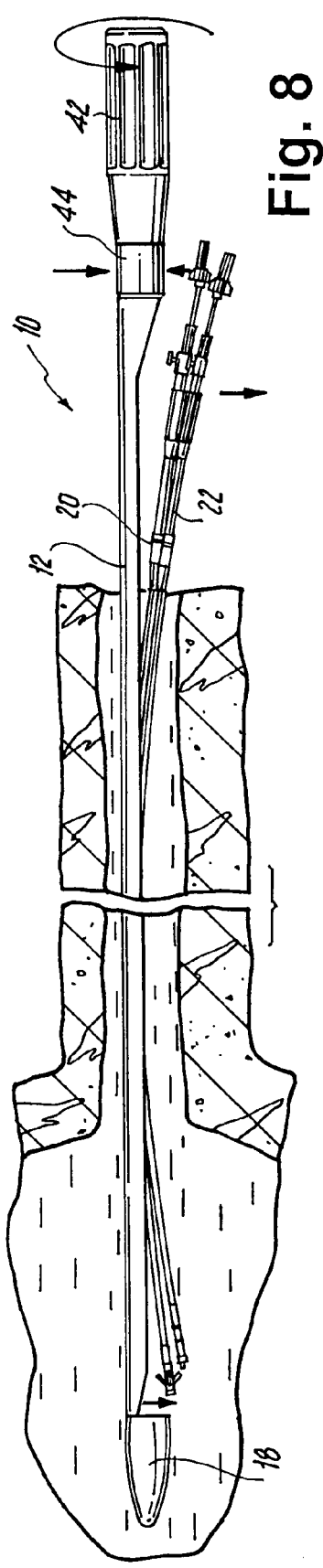

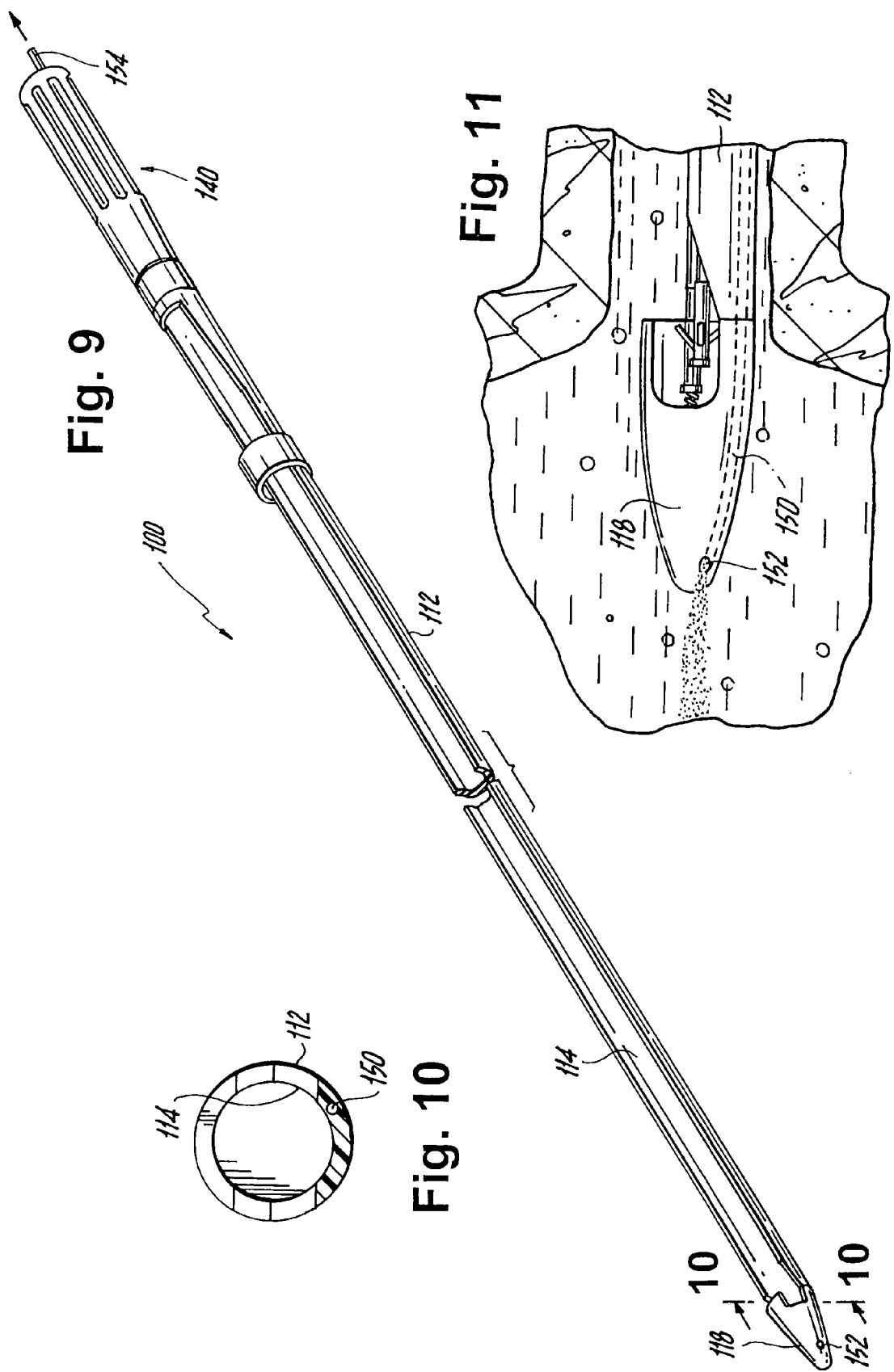

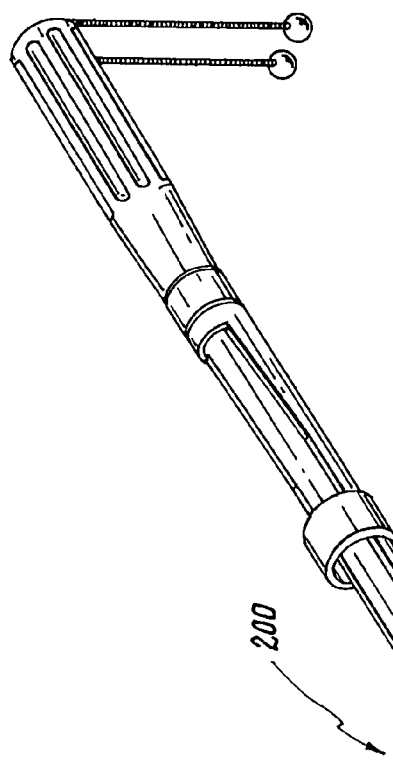
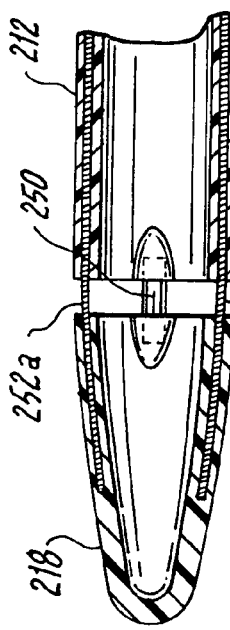
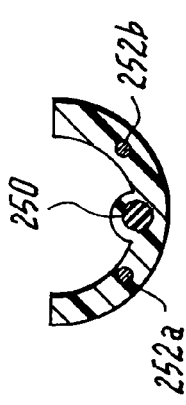
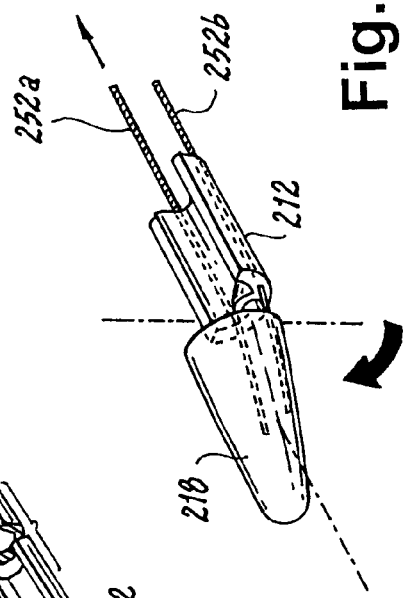
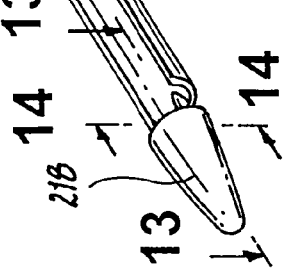

DEVICE AND METHOD FOR DELIVERING CARDIAC LEADS

CROSS-REFERENCE TO RELATED APPLICATIONS

The subject application claims the benefit of priority to U.S. Provisional Patent Application Ser. No. 60/397,203 filed Jul. 19, 2002, which is incorporated herein by reference in its entirety.

BACKGROUND OF THE INVENTION

1. Field of the Invention

The subject invention is directed to implantable cardiac stimulation leads, and more particularly, to a device and method for delivering one or more implantable cardiac leads to an implantation site while protecting the fixation mechanism at the distal end of the lead.

2. Background of the Related Art

Implantable cardiac stimulation leads, including epicardial and endocardial leads, are well known in the art. In general, these devices have an elongated flexible body with an electrode assembly at one end for contacting and stimulating cardiac tissue and a connector assembly at the other end for mating with an automated stimulation device, such as a pacemaker or defibrillator. The distal end of the lead can include a helical screw to facilitate active fixation of the lead tip or a plurality of flexible tines to facilitate passive fixation of the lead tip.

In the implantation of a cardiac device, and in the replacement of previously implanted cardiac leads, two or more transvenous cardiac leads are typically introduced through the venous system into the chambers or coronary sinus of the heart. To implant an endocardial lead within a heart chamber, a transvenous approach is typically utilized wherein the lead is inserted into and passed through the subclavian, jugular, or cephalic vein and through the superior vena cava into the right atrium or ventricle. A cover or retraction mechanism is generally used to protect the fixation helix on the lead tip during the transvenous advancement into the heart chamber. Once positioned, the helix is rotated into the myocardium to permanently fix the electrode.

Endocardial pacing and cardioversion/defibrillation leads have also been developed that are adapted to be advanced into the coronary sinus and coronary veins branching therefrom in order to locate the distal electrode(s) adjacent to the left ventricle or the left atrium. These leads are advanced through the superior vena cava, the right atrium, the valve of the coronary sinus, the coronary sinus, and into a coronary vein communicating with the coronary sinus, such as the great vein. Typically, coronary sinus leads do not employ any fixation mechanism and instead rely on the close confinement within these vessels to maintain each electrode at a desired site.

There are several known approaches for implanting cardiac leads introduced through the venous system into the right chambers or coronary sinus of the heart, as described above. One approach is disclosed in U.S. Pat. No. 5,246,014, which employs a catheter that surrounds the lead body and engages a distal screw-in electrode. The assembly is advanced to the desired site and rotated to screw the distal screw-in electrode into the myocardium of the right atrium or ventricle. The introducer can also be used to direct a cardiac lead into the coronary sinus opening.

Another approach is disclosed in U.S. Pat. No. 5,003,990, which relies on a guidewire and a carriage that releasably engages the distal screw-in electrode and is pushed along the guidewire as the lead body is pushed along a transvenous path. In yet another approach disclosed in U.S. Pat. No. 5,304,218 a cardiac lead is formed with a channel in the distal tip that receives a guidewire that has already been advanced through the path to the cardiac implantation site. The lead is pushed over the guidewire to the cardiac implantation site where the guidewire is withdrawn and the lead is either fixed in place or left at the cardiac implantation site.

U.S. Pat. No. 6,185,464 discloses a device for introducing and implanting a cardiac lead at an implantation site within a heart chamber or vessel. The device includes an elongated guide body and a tracking mechanism coupled with the distal end of the lead for receiving and slidingly engaging the guide. A pusher mechanism is provided, which engages the cardiac lead at or near the distal end thereof, to advance the guide body tracking mechanism and the cardiac lead distally along the guide body to the implantation site. Then, the lead body is released from the lead engaging mechanism and the pusher mechanism is retracted along with the pusher body. This device does not provide means to protect the fixation mechanism at the distal end of the lead, nor is it suited to deliver more than one lead at a time to the site of implantation.

It would be beneficial therefore, to provide a lead delivery device that facilitates the safe and efficient introduction of one or more endocardial cardiac leads into a heart chamber or vein while protecting the delicate fixation mechanism at the distal end of the lead.

SUMMARY OF THE INVENTION

The subject invention is directed to a new and useful device for delivering implantable cardiac leads to an implantation site within a chamber of the heart or an associated blood vessel. The device includes an elongated carrier body having opposed proximal and distal end portions and defining an interior channel for accommodating implantable cardiac leads, and means for securing the implantable cardiac leads within the interior channel of the carrier body during delivery to an implantation site. Preferably, the means for securing the implantable cardiac leads within the interior channel of the carrier body includes a collar mounted on the carrier body. More preferably, the collar is mounted for adjustable movement along the carrier body.

The lead delivery device further includes a journaled handle assembly for effectuating axial rotation of the carrier body to deploy the leads. In addition, the distal end portion of the carrier body is tapered to form a shroud configured to protect the distal end portion of the cardiac leads secured within the interior channel of the carrier body. In one embodiment of the invention, the protective shroud is collapsible to reduce its profile for removal from the implantation site. In another embodiment of the invention, the distal end portion of the carrier body includes electrically active mapping electrodes. In yet another embodiment of the subject invention, the distal end portion of the carrier body is adapted and configured for articulated movement.

The subject invention is also directed to a method for delivering implantable cardiac leads to a lead implantation site which includes the steps of providing a lead delivery device having an elongated carrier body defining an interior channel for accommodating an implantable cardiac leads, securing the implantable cardiac lead within the interior channel of the carrier body, guiding the carrier body to the implantation site, and releasing the cardiac lead from the interior channel of the carrier body at the implantation site.

Preferably, the method further includes the step of rotating the carrier body to deploy the cardiac lead at the implantation site.

These and other aspects of the cardiac lead delivery device and delivery method of the subject invention will become more readily apparent to those having ordinary skill in the art from the following detailed description of the invention taken in conjunction with the drawings.

BRIEF DESCRIPTION OF THE DRAWINGS

So that those having ordinary skill in the art to which the subject invention pertains will more readily understand how to make and use the cardiac lead delivery device disclosed herein, embodiments thereof will be described in detail below with reference to the drawings, wherein:

FIG. 1 is a perspective view of a preferred embodiment of the lead delivery device of the subject invention, which is illustrated along with a pair of implantable cardiac leads, where one lead is adapted for active fixation and other is adapted for passive fixation;

FIG. 2 is a perspective view of the distal end portion of the lead delivery device of FIG. 1 with the protective shroud detached from the carrier body;

FIG. 3 is a cross-sectional view taken along line 3—3 of FIG. 2 illustrating the journal arrangement for effecting axial rotation of the carrier body;

FIG. 4 is a perspective view of the lead delivery device of FIG. 1 with the implantable cardiac leads secured within the interior channel of the carrier body;

FIG. 5 is an illustration of the distal end portion of the lead delivery device as it advances through a blood vessel en route to the lead implantation site;

FIGS. 6 through 8 illustrate the various steps involved in the delivery of a pair of cardiac leads to the lead implantation site wherein:

FIG. 6 illustrates the arrival of the lead delivery device at the lead implantation site with the lead secured in the interior channel of the carrier body;

FIG. 7 illustrates the step of releasing the leads from a secured position within the interior channel of the carrier body by withdrawing the lead tips from the protective shroud and displacing the securement collar; and FIG. 8 illustrates the deployment of the leads from the interior channel of the carrier body by rotating the carrier body 180° about the longitudinal axis thereof;

FIG. 9 is a perspective view of another lead delivery device constructed in accordance with a preferred embodiment of the subject invention wherein a fluid delivery lumen extends through the carrier body to delivery an optical imaging fluid such as a dye or contrast fluid to the lead implantation site;

FIG. 10 is a cross-sectional view taken along line 10—10 of FIG. 9 illustrating the fluid delivery lumen formed in the carrier body;

FIG. 11 illustrates the distal end portion of the lead delivery device of FIG. 9, wherein an optical imaging fluid is dispatched from the exit port of the fluid delivery lumen;

FIG. 12 is a perspective view of another lead delivery device constructed in accordance with a preferred embodiment of the subject invention, wherein the distal end portion of the carrier body is configured for articulated movement;

FIG. 13 is a cross-sectional view taken along line 13—13 of FIG. 12 illustrating the flexible connection between the distal end portion of the carrier body and the remainder of the carrier body;

FIG. 14 is a cross-sectional view taken along line 14—14 of FIG. 12;

FIG. 15 is a perspective view of the distal end portion of the carrier body illustrating the range of articulated motion afforded thereto by the flexible connection;

DETAILED DESCRIPTION OF PREFERRED EMBODIMENTS

Figure 16:
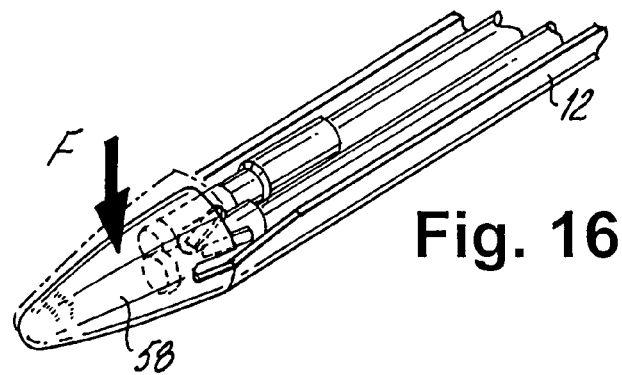
FIG. 16 is a perspective view of the distal end portion of another embodiment of the lead delivery device of the subject invention, wherein the protective shroud is collapsible.
Figure 17:
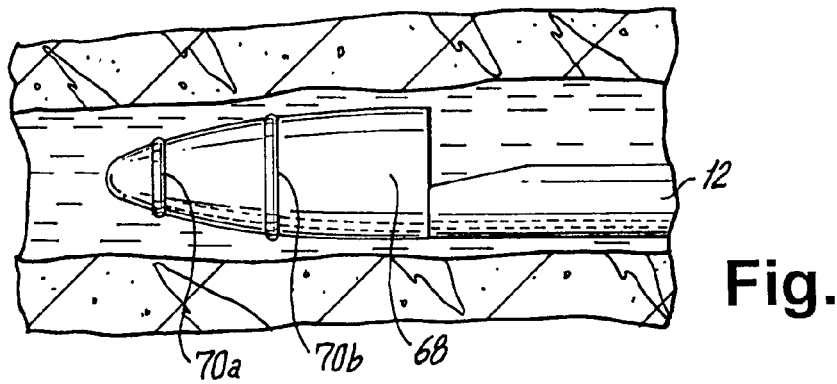
FIG. 17 is a side elevational view of the distal end portion of another embodiment of the lead delivery device of the subject invention, wherein the protective shroud has spaced apart mapping electrodes.

In the description which follows, the term "proximal" refers to the end of the lead delivery device which is farthest from the implantation site, while the term "distal" refers to the end of the lead delivery device which is nearest to the site of implantation.

Referring now to the drawings wherein like reference numerals identify similar structural features of the subject invention, there is illustrated in FIG. 1 a lead delivery device constructed in accordance with a preferred embodiment of the subject invention and designated generally by reference numeral 10. Lead delivery device 10 is adapted and configured to deliver one or more implantable cardiac leads, along a transvenous path, to a lead implantation site within a chamber of the heart or an associated blood vessel, while protecting the fixation mechanism and electrode assembly located at the distal end of the lead.

Referring to FIG. 1, lead delivery device 10 includes an elongated, flexible carrier body 12 formed from a lightweight, bio-compatible plastic or rubber material and having opposed proximal and distal end portions and defining an interior channel 14 for accommodating one or more implantable cardiac lead. Lead body 12 is dimensioned to accommodate cardiac leads of conventional length and diameter, such as cardiac leads ranging from about 45 cm to about 58 cm in length, and ranging up to 10F in diameter.

The interior channel 14 of lead body 12 preferably has a U-shaped cross-section. Although, it is envisioned that the interior channel 14 can be provided with two or more channels, each for accommodating a respective cardiac lead. Preferably, the peripheral wall of the interior channel 14 is relatively high at the proximal end portion of carrier body 12 to accommodate and more completely enclose the lead connectors and tool handles that may be associated with the leads, as best seen in FIG. 4. Two implantable cardiac leads are illustrated in FIG. 1. These include a first cardiac lead 20 having a fixation helix 24 at the distal end thereof to facilitate active fixation of the lead at the implantation site, and a second cardiac lead 22 having a plurality of flexible tines 26 at the distal end thereof to facilitate passive fixation of the lead at an implantation site.

Lead delivery device 10 further includes an annular collar 30 for securing the implantable cardiac leads 20, 22 within the interior channel 14 of the carrier body 12 during delivery to an implantation site, as illustrated in FIG. 4. The collar 30 may be formed form a substantially rigid, flexible or expandable biocompatible material. As best seen in FIG. 7, collar 30 is preferably mounted for adjustable movement along the carrier body 12 between a first position wherein the cardiac leads 20, 22 are retained securely within the interior channel 14 of carrier body 12 and a released position, proximal to the retained position, wherein the leads 20, 22 are free for deployment from the interior channel 14 of carrier body 12. It is envisioned that collar 30 may be entirely or partially removable from the carrier body 12 to effectuate deployment of the leads at the implantation site. It is also envisioned that more than one collar may be employed on the carrier body for securing the leads during delivery.

The distal end portion of lead delivery device 10 defines a protective shroud 18 for shielding the distal end portion of the cardiac leads retained within the interior channel 14 of carrier body 12, as illustrated in FIG. 5. The shroud 18 is generally tapered in configuration to present an atraumatic surface to a blood vessel through which the lead delivery device 10 is passing. The protective shroud 18 may be integrally-formed with the carrier body 12 or attached to the distal end of the carrier body, as illustrated in FIG. 2, by an adhesive or other known fixation method. The shroud 18 is preferably formed with a lateral opening 18a so that leads may be easily loaded into the lead delivery device 10 prior to introducing the device into a blood vessel.

Referring once again to FIG. 1, the carrier body 12 of lead delivery device 10 is adapted and configured for axial rotation to facilitate the deployment of the leads 20, 22 from the interior channel 14 after the securement collar 30 has been moved to a released position or removed entirely or partially from the carrier body 12 (see FIGS. 6 through 8). More particularly, lead delivery device 10 has a journaled handle assembly 40 at the proximal end thereof for effectuating the axial rotation of the carrier body 12. The handle assembly includes a fluted handle member 42 which depends proximally from the carrier body 12 and an annular retention collar 44. As best seen in FIG. 3, retention collar 44 is supported on a journal 46 defined by a circumferential region of reduced diameter formed in the proximal end of carrier body 12.

Referring now to FIGS. 6 through 8, there is illustrated the various steps involved in the delivery of a pair of cardiac leads 20, 22 to a lead implantation site within the chamber of the heart, by way of a transvenous approach. Initially, as illustrated in FIG. 6, when the distal end portion of the lead delivery device 10 arrives at or near the lead implantation site, the leads 20, 22 are secured in the interior channel 14 of the carrier body 12 by securement collar 30. Thereupon, as shown in FIG. 7, the securement collar 30 is moved to a releasing position or simply removed from the carrier body to free the leads. It is envisioned that the collar could be split into two halves along a predefined parting line for removal, stretched if formed froin an elastic material or simply severed with a cutting tool and discarded.

Once the collar 30 has been moved to a releasing position or simply removed from the device, the leads may be drawn in a proximal direction so as to clear the distal end portions of the leads from the protective shroud 18 at the distal end of the carrier body 12. Thereafter, retention collar 44 is grasped by applying an inwardly directed force "F", and the fluted handle member 42 is rotated so that the carrier body 12 rotates 180° relative to the longitudinal axis thereof within journal 46. At such a time, leads 20, 22 are deployed from the interior channel 14 of carrier body 12, as illustrated in FIG. 8. Once the leads have been deployed, the delivery device 10 may be withdrawn from the implantation site. It is envisioned that the lead delivery device 10 of the subject invention could be designed for discardment after first use or adapted to be cleaned and sterilized for subsequent use in multiple implantation procedures.

Referring to FIGS. 9 through 11, there is illustrated another lead delivery device constructed in accordance with a preferred embodiment of the subject invention and designated generally by reference numeral 100. Lead delivery device 100 is substantially identical to lead delivery device 10, except that lead delivery device 100 includes at least one internal fluid delivery lumen 150 that extends through the carrier body 112, below the interior channel 114, from the handle assembly 140 at the proximal end of the device to the protective shroud 118 at the distal end of the device. The fluid delivery lumen 150 has an exit port 152 adjacent the shroud tip and is adapted and configured to deliver an optical imaging fluid, such as dye or contrast media, to the implantation site to ensure accurate placement of the lead electrodes relative to the cardiac tissue to be stimulated thereby. A connective fitting 154 is preferably provided at the proximal end of handle assembly 140 for receiving or communicating with a source of optical imaging fluid.

Referring now to FIGS. 12 through 15, there is illustrated yet another lead delivery device constructed in accordance with a preferred embodiment of the subject invention and designated generally by reference numeral 200. Lead delivery device 200 is also substantially identical to lead delivery device 10, except that shrouded portion 218 of the carrier body 212 is adapted and configured for articulated movement to enable the device to traverse tortuous blood vessels or obstructions en route to the implantation site. More particularly, the shrouded portion 218 of lead delivery device 200 is attached to the distal end of carrier body 212 by a flexible hinge 250 or a similar structural feature such as a linkage or ball joint. Movement of the articulating shrouded portion 218 of lead delivery device 200 is controlled from the proximal end of the device by a pair of actuation cables 252a, 252b, as shown in FIG. 15, or by a similar mechanism such as a multi-bar linkage or axial screw.

Figure 18:
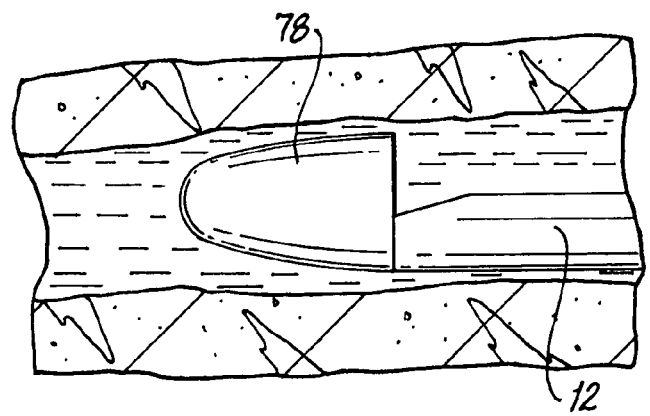
FIG. 18 is a side elevational view of the distal end portion of another embodiment of the lead delivery device of the subject invention, wherein the protective shroud has a rounded tip.
Figure 19:
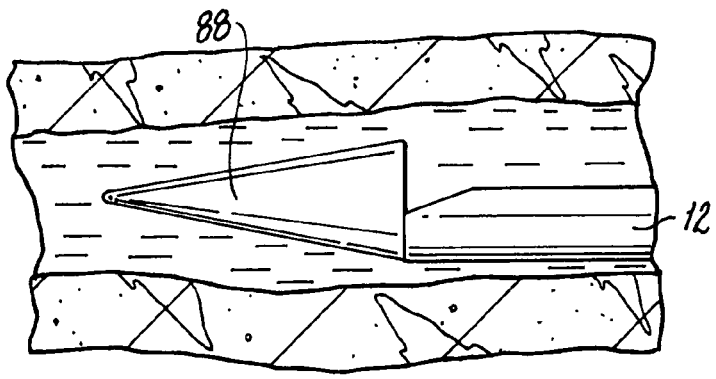
FIG. 19 is a side elevational view of the distal end portion of another embodiment of the lead delivery device of the subject invention, wherein the protective shroud has a conical tip.

As illustrated in FIGS. 16 through 19, the protective shroud of the lead delivery device 10 of the subject invention can take many different forms. For example, in one embodiment of the subject invention shown in FIG. 16, the lead delivery device has a collapsible shroud 58. The collapsible shroud 58 presents a reduced profile when subjected to a compressive force "F" so as to ease removal of the device from the implantation site after the leads have been deployed. In another embodiment of the subject invention shown in FIG. 17, the lead delivery device has a protective shroud 68 with axially spaced apart electrically active mapping electrodes 70a, 70b for sensing the position of the delivery device, to ensure safe placement of the leads at the implantation site. In the alternative, radiopaque bands formed from barium sulfate or a similar material may be utilized to provide visually observable placement of the delivery device. As shown in FIG. 18, another delivery device has a shroud 78 with a rounded profile, while yet another delivery device has a shroud 88 that has a generally conical configuration.

Although the lead delivery device of the subject invention has been described with respect to preferred embodiments, those skilled in the art will readily appreciate that changes and modifications may be made thereto without departing from the spirit and scope of the subject invention as defined by the appended claims.

What is claimed is:

1. A device for delivering implantable cardiac leads to an implantation site comprising:
   a) an elongated carrier body having opposed proximal and distal end portions and defining an open interior channel having a generally U-shaped cross-section for accommodating at least one implantable cardiac lead, wherein the distal end portion of the carrier body is tapered to form a shroud to protect the distal end portion of the at least one cardiac lead and wherein the shroud is collapsible to reduce the profile thereof for removal from the implantation site; and
   b) an adjustable collar mounted for movement along the carrier body for releasably securing the at least one implantable cardiac lead within the open interior channel of the carrier body during delivery to the implantation site.

2. A device as recited in claim 1, wherein the distal end portion of the carrier body includes electrically active mapping electrodes.

3. A device as recited in claim 1, wherein the distal end portion of the carrier body is adapted and configured for articulated movement.

4. A device as recited in claim 1, further comprising means operatively associated with the proximal end portion of the carrier body for effectuating articulated movement of the distal end portion of the carrier body.

5. A device as recited in claim 1, further comprising a journaled handle assembly for effectuating axial rotation of the carrier body.

* * * * *